(12) United States Patent
Nakamura (10) Patent No.: US 8,505,276 B2
(45) Date of Patent: Aug. 13, 2013

(54) PARTICULATE MATTER MEASUREMENT DEVICE

(75) Inventor: Hiroshi Nakamura, Kyoto (JP)

(73) Assignee: Horiba, Ltd., Kyoto (JP)

(*) Notice: Subject to any disclaimer, the term of this patent is extended or adjusted under 35 U.S.C. 154(b) by 322 days.

(21) Appl. No.: 13/054,349

(22) PCT Filed: Jul. 13, 2009

(86) PCT No.: PCT/JP2009/062675
§ 371 (c)(1),
(2), (4) Date: Jan. 14, 2011

(87) PCT Pub. No.: WO2010/007965
PCT Pub. Date: Jan. 21, 2010

(65) Prior Publication Data
US 2011/0120096 A1    May 26, 2011

(30) Foreign Application Priority Data
Jul. 16, 2008  (JP) .................................. 2008-184516

(51) Int. Cl.
*F01N 3/00* (2006.01)
*G01N 33/497* (2006.01)
*G01N 7/00* (2006.01)
*G01N 37/00* (2006.01)
*G01N 31/00* (2006.01)

(52) U.S. Cl.
USPC .......... 60/276; 73/23.31; 73/23.33; 73/28.01; 702/26

(58) Field of Classification Search
USPC .................. 60/276, 288, 289, 311; 73/19.12, 73/23.2, 23.31, 23.33, 28.01, 28.02; 702/24, 702/26, 29
See application file for complete search history.

(56) References Cited

U.S. PATENT DOCUMENTS

| | | | |
|---|---|---|---|
| 6,370,936 B1* | 4/2002 | Yamagishi et al. | 73/1.35 |
| 6,796,165 B2* | 9/2004 | Abdul-Khalek | 73/28.01 |
| 2002/0020232 A1* | 2/2002 | Yamagishi et al. | 73/863.11 |
| 2007/0068236 A1 | 3/2007 | Wei et al. | |
| 2009/0287424 A1* | 11/2009 | Nakamura | 702/24 |

FOREIGN PATENT DOCUMENTS

| | | |
|---|---|---|
| CN | 101113947 A | 1/2008 |
| JP | 2006506640 T | 2/2006 |
| JP | 2008507698 A3 | 3/2008 |
| JP | 2008157692 A | 7/2008 |
| WO | 2007041274 A2 | 4/2007 |

* cited by examiner

*Primary Examiner* — Kenneth Bomberg
*Assistant Examiner* — Audrey K Bradley
(74) *Attorney, Agent, or Firm* — Brooks Kushman P.C.

(57) ABSTRACT

Disclosed is a particulate matter measurement device that continuously measures changes in a mass of particulate matters contained in an exhaust gas under dynamic operating conditions. The device dilutes and separates the flow of exhaust gas while an engine is operating. The particulate matters contained in one of the exhaust gas streams are collected by a collection filter to measure the mass and the remainder is measured by a mass-related value measurement. Then, time series change data for the mass of the particulate matter are found based on correlations of the individual measured data. With this arrangement, the flow volume of the dilute exhaust gas that passes through the collection filter and the flow volume of the dilute exhaust gas that is introduced into the mass-related value measurement device are ensured by adjusting the flow volume of the diluting gas that dilutes the exhaust gas.

12 Claims, 6 Drawing Sheets

PARTICULATE MATTER MEASUREMENT DEVICE

FIELD OF THE ART

This invention relates to a particulate matter measurement device that measures a mass of particulate matters contained in an exhaust gas of an engine.

BACKGROUND ART

As a method for measuring a mass of particulate matters (PM: in this specification hereinafter also called as PM) as being one of emission matters from an engine known is a filter mass method. The filter mass method is a method for collecting the PM by arranging a collection filter on a flow channel of an exhaust gas from an engine and measuring a mass of the collected PM by the use of a balance or the like. Since the filter mass method can directly measure a mass of the PM in which practically exists no reference material whose physicality can be specified, it is possible to expect certainly and correctness of the measurement. As a result, among measurement devices using the filter mass method used for an exhaust gas test presently on a standard basis is a constant volume sampler (CVS) that dilutes all amount of the exhaust gas from an engine and conducts an analysis.

Meanwhile, with the view of further improving engine performance or an environmental problem there is recently a request that a time series change of the PM emission amount while the engine is dynamically in operation on a road or the like be measured. However, since the filter mass method is, so called, a batch-type measurement method wherein only an integrated mass of the PM discharged during a certain period can be measured, it is not possible to know how the mass of the PM changes from moment to moment in accordance with a dynamic driving situation.

Then as an alternative method for the filter mass method proposed or developed are an FID (Flame Ionization Detector), an ELPI (Electric Low Pressure Impactor), an SMPS (Scanning Mobility Particle Sizer), a DCS (Diffusion Charger Sensor) (Patent document 1). The FID is to measure a number of carbon atoms in a sample gas, and the ELPI and SMPS are to count a number of particles. In addition, the DCS is to charge a surface of the particles and to measure a charged amount.

In accordance with these devices, although it is possible to conduct a measurement during a road travel, however, the measurement is to measure the number of carbon atoms, the number of the PM, or the surface area of the particles, and is not to measure the mass of the PM directly. As a result, in order to obtain the mass of the PM from these measurement results, it is necessary to obtain a correlation between the measurement result and a measurement result by the collection filter measurement method conducted under the same condition, and to calculate the mass of the PM based on the correlation.

Then, it can be conceived that a correlation between a measurement result by the filter mass method and a measurement result by the ELPI method in each driving state of the engine is previously obtained, and a dynamic change of the mass of the PM is calculated by applying this correlation to the measurement result by the ELPI during the road travel.

However, since this correlation is consistently a correlation at a time when each driving state of the engine is kept in a constant static state, it is a little unreasonable that this correlation is directly applied to a case of the road travel such that the dynamic driving is conducted and that the result is estimated as the actual dynamic change of the mass of the PM.

PRIOR ART DOCUMENTS

Patent Document

Patent document 1: Japan patent laid-open number 2006-506640

DISCLOSURE OF THE INVENTION

Problems to be Solved by the Invention

The present claimed invention intends to solve all of the problems and a main object of this invention is to continuously measure a change of the mass of the PM contained in the exhaust gas under a dynamic driving situation such as a road travel with a simple arrangement.

Means to Solve the Problems

More specifically, the particulate matter measurement device in accordance with the invention described in claim 1, is characterized by comprising the following arrangement.
(1) A dilutor that is connected to an exhaust pipe of an automobile and connected to a dilution gas introducing inlet and that mixes an exhaust gas from an engine of the automobile with a dilution gas so as to dilute the exhaust gas.
(2) A mass-related value measurement device into which a part of the diluted exhaust gas diluted by the dilutor is introduced and that continuously measures a mass-related value indirectly indicating a mass of particulate matters contained in the diluted exhaust gas.
(3) A collection filter through which the remainder of the diluted exhaust gas passes and that collects the particulate matters contained in the remainder of the diluted exhaust gas.
(4) A dilution gas flow rate adjusting device that adjusts a flow rate of the dilution gas introduced into the dilutor.
(5) A filter passing flow rate adjusting device that adjusts a flow rate of the diluted exhaust gas passing the collection filter.
(6) A flow rate measurement device that measures the flow rate of the diluted exhaust gas introduced into the mass-related value measurement device.
(7) A control part that keeps a flow rate of the diluted exhaust gas passing the collection filter at a constant value by controlling the filter passing flow rate adjusting device and that secures a necessary flow rate of the diluted exhaust gas introduced into the mass-related value measurement device by controlling the dilution gas flow rate adjusting device.
(8) An information processing part that calculates a correlation between a mass measurement value of the particulate matters collected by the collection filter during a predetermined period while the engine is in operation and a time integrated value of the mass-related value measurement data during the predetermined period as being a time series change data of the mass-related value measured by the mass-related value measurement device and that converts the mass-related value measurement data to the time series change data of the mass of the particulate matters based on the correlation.

In accordance with this arrangement, since the mass-related value measurement data indirectly indicating the mass of the PM and continuous in terms of time series and measured while the engine is in operation is calibrated based on the correlation of the amount of the PM discharged while the engine is in operation and directly collected by the collection filter, and converted to the continuous time series data of the mass of the PM, it is possible to obtain a highly reliable continuous time series data of the mass of the PM unlike a case wherein the fixed correlation obtained under a static condition completely different from a dynamic condition such as running on a road.

In addition, as hardware, there is no need of any component such as an additional mechanism for introducing air other than the mass-related value measurement device additionally arranged to a dilution exhaust gas piping for the PM collection mechanism using a conventional collection filter, it is possible to structure the hardware extremely easy. Furthermore, since the flow rate passing the collection filter is made constant on a constant basis and the flow rate required for sampling by the mass-related value measurement device is secured to be constant by controlling the flow rate of the diluted exhaust gas that is a mixture of the exhaust gas and the air with a process of increasing or decreasing the flow rate of the air for dilution, it is possible to preferably avoid a measurement error due to lack of the flow rate.

In addition, the particulate matter measurement device in accordance with the invention described in claim 2, is characterized by comprising the following arrangement.

(1) A dilutor that is connected to an exhaust pipe of an automobile and connected to a dilution gas introducing inlet and that mixes an exhaust gas from an engine of the automobile with a dilution gas so as to dilute the exhaust gas.
(2) A mass-related value measurement device into which a part of the diluted exhaust gas diluted by the dilutor is introduced and that continuously measures a mass-related value indirectly indicating a mass of particulate matters contained in the diluted exhaust gas.
(3) A collection filter through which the remainder of the diluted exhaust gas passes and that collects the particulate matters contained in the remainder of the diluted exhaust gas.
(4) A dilution gas flow rate adjusting device that adjusts a flow rate of the dilution gas introduced into the dilutor.
(5) A filter passing flow rate adjusting device that adjusts a flow rate of the diluted exhaust gas passing the collection filter.
(6) A flow rate measurement device that measures the flow rate of the diluted exhaust gas introduced into the mass-related value measurement device.
(7) A control part that keeps a sum of the flow rate of the diluted exhaust gas introduced into the mass-related value measurement device and the flow rate of the diluted exhaust gas passing the collection filter at a constant value by controlling the filter passing flow rate adjusting device based on the flow rate of the diluted exhaust gas introduced into the mass-related value measurement device.
(8) An information processing part that calculates a correlation between a mass measurement value of the particulate matters collected by the collection filter during a predetermined period while the engine is in operation and a time integrated value of the mass-related value measurement data during the predetermined period as being a time series change data of the mass-related value measured by the mass-related value measurement device and that converts the mass-related value measurement data to the time series change data of the mass of the particulate matters based on the correlation.

In accordance with this arrangement, similar to the invention of claim 1, it is possible to obtain the highly reliable continuous time series data of the mass of the PM and to produce an effect that the arrangement can be realized extremely easy as well.

The particulate matter measurement device in accordance with the invention of claim 3 is so arranged to be loaded on the automobile actually running on a road and to measure the particulate matters in the exhaust gas while the engine is dynamically driving and the automobile is running. With this arrangement, the above-mentioned effect becomes especially remarkable. In addition, in order to load the particulate matter measurement device on the automobile, it is more preferable that the collected particulate matters are burned by applying heat to the collection filter and the mass of the particulate matters are measured from a component of the burned gas.

A physicality indirectly indicating the mass of the particulate matters is a surface area, a number or a particle size distribution of the particulate matters.

Effect of the Invention

The above-mentioned invention in accordance with each claim obtains the correlation between the continuous time series data indirectly indicating the mass of the PM measured while the engine is in operation and the measurement result directly indicating the total mass of the PM discharged while the engine is in operation every time the measurement is conducted, and calculates the continuous time series data of the mass of the PM based on the correlation.

As a result, it is possible to obtain the highly reliable continuous time series data of the mass of the PM unlike a case wherein the fixed correlation obtained under a static condition completely different from a dynamic condition such as running on a road.

In addition, as hardware, there is no need of any component such as an additional mechanism for introducing air other than the mass-related value measurement device additionally arranged to a dilution exhaust gas piping for the PM collection mechanism using a conventional collection filter, it is possible to structure the hardware extremely easy. Especially in accordance with the invention of claim 1, since the flow rate passing the collection filter is made constant on a constant basis and the flow rate required for sampling by the mass-related value measurement device is secured to be constant by controlling the flow rate of the diluted exhaust gas that is a mixture of the exhaust gas and the air with a process of increasing or decreasing the flow rate of the air for dilution, it is possible to preferably avoid a measurement error due to lack of the flow rate.

BEST MODES OF EMBODYING THE INVENTION

One embodiment of this invention will be explained with reference to drawings.

First Embodiment

Figure 1:
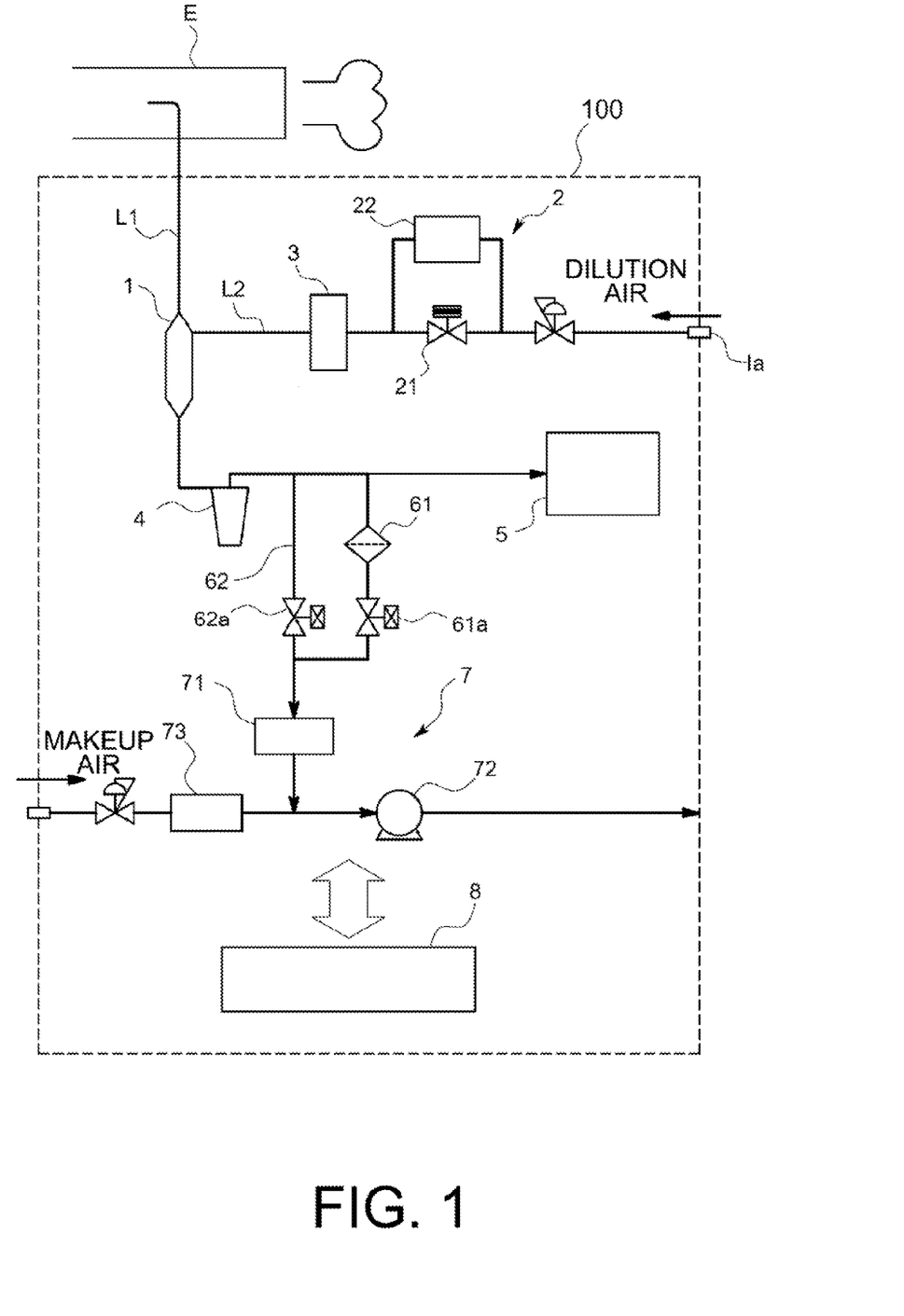
FIG. 1 is a pattern general overall view showing a particulate matter measurement device in accordance with one embodiment of this invention.

FIG. 1 shows an overall general view of a particulate matter measurement device 100 in accordance with this embodiment. The particulate matter measurement device 100 is loaded on an automobile and measures a mass concentration of particulate matters contained in an exhaust gas emitted from an engine as being an internal combustion engine while the automobile is running on a road.

In FIG. 1, a code (E) is an exhaust pipe of the automobile, a code 1 is a mixer that mixes the exhaust gas with air as being a dilution gas and produces a diluted exhaust gas. An exhaust gas introduction pipe L1 that is connected to the exhaust pipe (E) and into which a part of the exhaust gas is introduced is connected to the mixer 1 and an air introduction pipe L2 whose one end is exposed to the air as a dilution gas introduction inlet (Ia) is connected to the mixer 1. A dilution gas flow rate adjusting device 2 and a dilution gas flow meter 3 are arranged in series in the middle of the air introduction pipe L2. The dilution gas flow rate adjusting device 2 has an arrangement wherein a piezoelectric valve 21 and a critical flow rate orifice 22 are arranged in parallel and controls an air flow rate flowing in the air introduction pipe L2 by the use of a command signal from a computer 8, to be described later, by a constant dilution method or a proportional dilution method. The dilution gas flow meter 3 is, for example, a venturi flow rate meter.

The piping is so arranged, as shown in FIG. 1, the diluted exhaust gas mixed and diluted with the air by the mixer 1 passes a cyclone 4 for removing dust and a part of the diluted exhaust gas is introduced into the mass-related value measurement device 5 and the remainder of the diluted exhaust gas is introduced into the collection filter 61.

Figure 2:
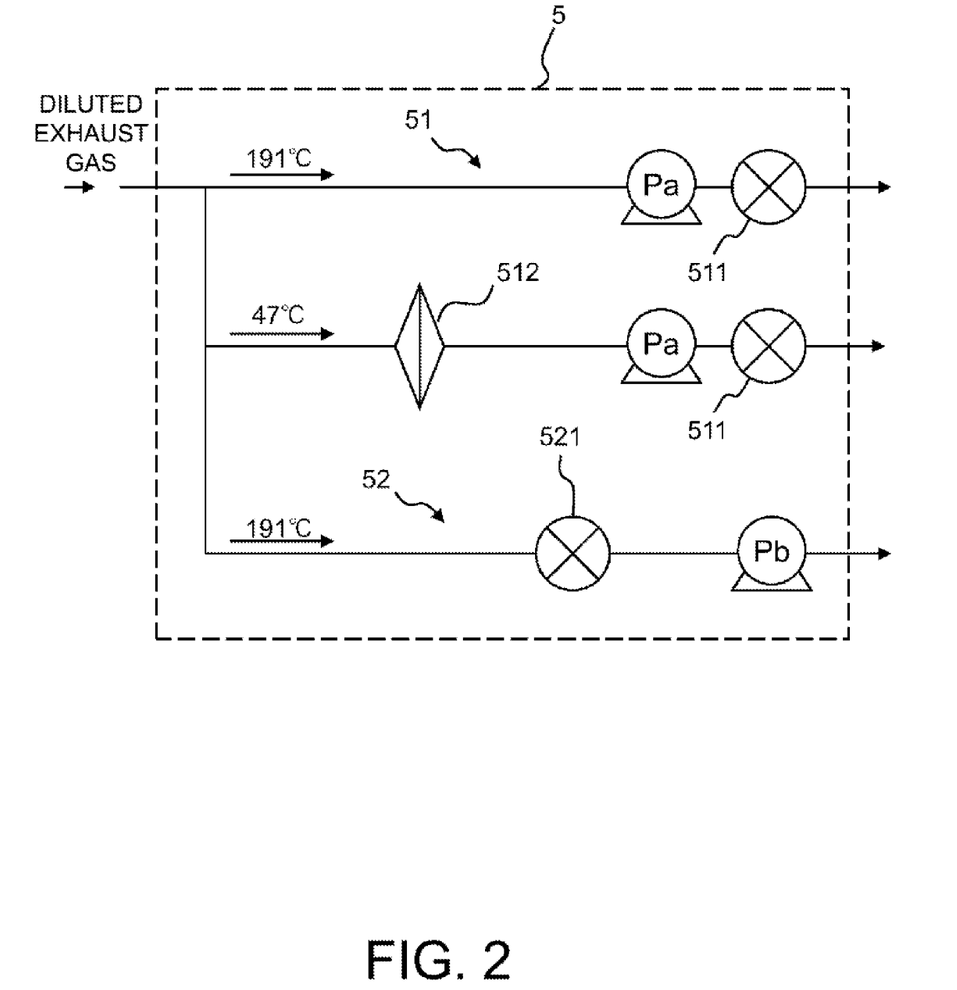
FIG. 2 is an overall view showing a simplified internal structure of a mass-related value measurement device in this embodiment.

The mass-related value measurement device 5 continuously measures physical properties that indirectly indicate the mass of the particulate matters and outputs a mass-related value data as being a time series change data. Concretely, the mass-related value measurement device 5, whose simplified internal structure is shown in FIG. 2, is so arranged that an SOF measurement system 51 that can continuously measure a soluble organic fraction (SOF, mainly hydrocarbon) and a soot measurement system 52 that can continuously measure soot are arranged in parallel, wherein the SOF and the soot can be conceived as a main component of the particulate matters. The SOF measurement system 51 is, as shown in FIG. 2, provided with two hydrogen flame ionization detectors 511, 511 arranged in parallel, and is so arranged to divide and introduce the diluted exhaust gas introduced into the SOF measurement system 51 into each of the hydrogen flame ionization detectors 511, 511. In FIG. 2, a code (Pa) is a suction pump and a code 512 is a removing filter.

The hydrocarbon (SOF) contained in the diluted exhaust gas is introduced into one of the hydrogen flame ionization detectors 511 as it is without being solidified or liquefied by keeping a piping that reaches the hydrogen flame ionization detector 511 at a high temperature (about 191° C.) by means of a temperature adjustor, not shown in drawings.

In addition, the hydrocarbon (SOF) that is solidified or liquefied at a low temperature is removed by the removing filter 512 and is not introduced into the other hydrogen flame ionization detector 511 by keeping a piping that reaches the hydrogen flame ionization detector 511 at a low temperature (47° C.±5° C.).

The hydrogen flame ionization detector 511 ionizes hydrocarbon contained in the introduced diluted exhaust gas, and then detects and outputs its ionic current continuously in real time. Since the value of the detected signal is correlated with a mass of the SOF, it is possible to estimate and calculate the mass of the SOF based on the value of the detected signal.

With this embodiment, since a flow rate introduced into each of the hydrogen flame ionization detector 511 can be measured by a flow meter, not shown in drawings, a computer, to be described later, estimates and calculates the mass of the SOF respectively based on the above-mentioned correlation from the value of the detected signal of each hydrogen flame ionization detector 511, and then divides the calculated mass of the SOF by a flow rate and a dilution ratio, and the difference between them is obtained and finally the mass of the SOF contained in a unit flow of the exhaust gas is estimated and calculated.

The soot measurement system 52 is, as shown in FIG. 2, provided with a DC sensor 521 and a suction pump (Pb) arranged in series, and a piping that reaches the DC sensor 521 is kept at a predetermined temperature (about 191° C.) by means of a temperature adjustor, not shown in drawings. This is to volatilize the SOF (especially the SOF attached to the soot) contained in the diluted exhaust gas and to introduce only the soot to the DC sensor 521.

The DC sensor 521 measures a surface area of the soot continuously in real time by making use of a diffusion charge method. The DC sensor 521 gives an charge proportional to a surface area of the soot contained in the diluted exhaust gas to the soot by means of the corona discharge, and then detects and outputs an amount of an electric current due to the charge. Since the charge amount is proportional to the surface area of the sooth, the value of the detected signal indicates the surface area of the soot. Since there is a predetermined correlation between the surface area of the soot and the mass of the soot, it is possible to estimate and calculate the mass of the soot from the value of the detected signal.

With this embodiment, since the flow rate introduced into the DC sensor 521 can be measured by the flow meter, not shown in drawings, the computer 8, to be described later, estimates and calculates the mass of the soot from the detected signal of the DC sensor 521 based on the above-mentioned correlation and then divides the calculated mass of the soot by a flow rate and a dilution ratio, and finally the mass of the soot contained in a unit flow of the exhaust gas is estimated and calculated.

Next, the collection filter 61 will be explained. The collection filter 61 is a known filter determined by a regulation (measurement reference) of the exhaust gas measurement. In order to measure the mass of the particulate matters collected by the collection filter 61, a conventional balance method may be used. However, with the balance method, there are problems that it takes time to conduct measurement since a procedure of mounting or dismounting the collection filter 61 is necessary and that the collection filter 61 might absorb moisture. Then in this embodiment, for example, a filter combustion method wherein a high correlation is established with the balance method is used. The filter combustion method is to apply heat to the filter 61 so as to burn only the collected particulate matters and to measure a component and an amount of the combustion gas.

In FIG. 1, a code 62 arranged in parallel with the collection filter 61 is a bypass flow channel to secure a flow of the diluted exhaust gas in case that the diluted exhaust gas is not introduced into the collection filter 61. For example, in case that the diluted exhaust gas is not introduced into the collection filter 61 during a period while the particulate matters is not collected, an open/close valve 61a at a side of the collection filter 61 is closed and an open/close valve 61b at a side of the bypass flow channel 62 is open. Contrarily, in case of collecting the particulate matters, the open/close valve 61a at the side of the collection filter 61 is open and the open/close valve 61b at the side of the bypass flow channel 62 is closed.

The flow channel of the diluted exhaust gas passing the collection filter 61 can be adjusted by a filter passing flow rate adjusting device 7 arranged on the downstream of the collection filter 61. The filter passing flow rate adjusting device 7 comprises, as shown in FIG. 1, a venturi flow meter 71 arranged on the downstream of the collection filter 61 in serial, a suction pump 72 and a mass flow controller 73, each of which is arranged on the downstream of the venturi flow meter 71. The filter passing flow rate adjusting device 7 is so arranged that a back pressure of the venturi flow mater 71 is adjusted by adjusting a flow rate of the mass flow controller 73 so that a flow rate of the diluted exhaust gas flowing in the venturi flow meter 71 can be adjusted.

Figure 3:
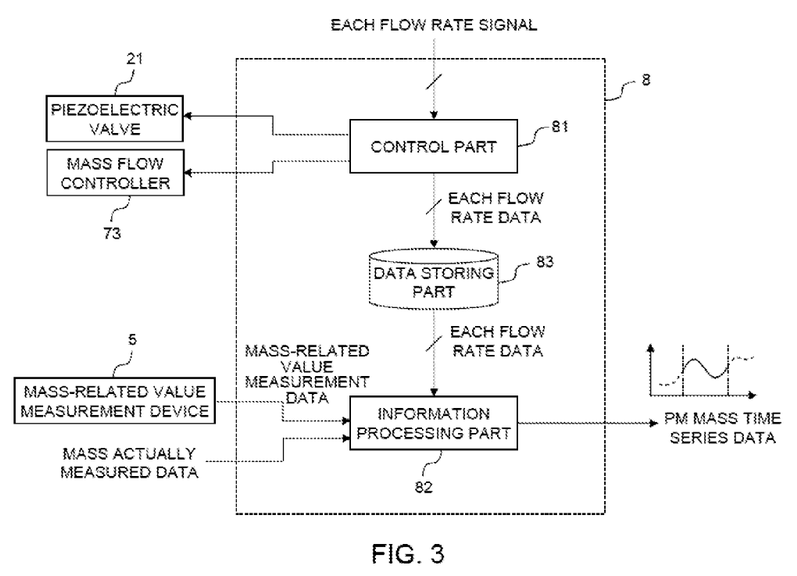
FIG. 3 is a functional block diagram showing a function of a computer of this embodiment.

Furthermore, as mentioned above, in this embodiment provided is a general purpose or dedicated computer 8 comprising a CPU, a memory, an input/output interface. This computer 8 functions as a control part 81 and an information processing part 82 as shown in FIG. 3 by operating the CPU and its peripheral devices based on a predetermined program stored in the memory.

The particulate matter measurement device 100 having the above-mentioned arrangement is loaded on an automobile as mentioned above, and is operated in a state that the automobile actually runs on a road. Detail of the operation of the particulate matter measurement device 100 while the automobile is actually running will be explained together with an explanation of functions of the control part 81 and the information processing part 82.

The control part 81 controls the back pressure of the venturi flow meter 71 by transmitting a command signal to the mass flow controller 73 of the filter passing flow rate adjusting device 7 to control a flow rate passing the mass flow controller 73 and keeps the flow rate (hereinafter also called as the filter passing flow rate) of the diluted exhaust gas passing the collection filter 61 at a constant value determined by the regulation (step S1 in FIG. 4).

Meanwhile, the control part 81 receives a flow rate signal from a flow meter, not shown in drawings, mounted on the exhaust pipe (E) of the engine, a flow rate signal from the venturi flow meter 3 that measures an air introducing flow rate, and a flow rate signal from a flow meter, not shown in drawings, arranged on the mass-related value measurement device 5, and stores data regarding an exhaust gas total flow rate, an introducing flow rate of the dilution air (hereinafter also called as the air introducing flow rate), and a flow rate of the diluted exhaust gas (hereinafter also called as a sensor use flow rate) introduced into the mass-related value measurement device 5 shown by each of the flow rate signals in the data storing part 83 each of which is set in the memory (step S2 in FIG. 4).

Figure 4:
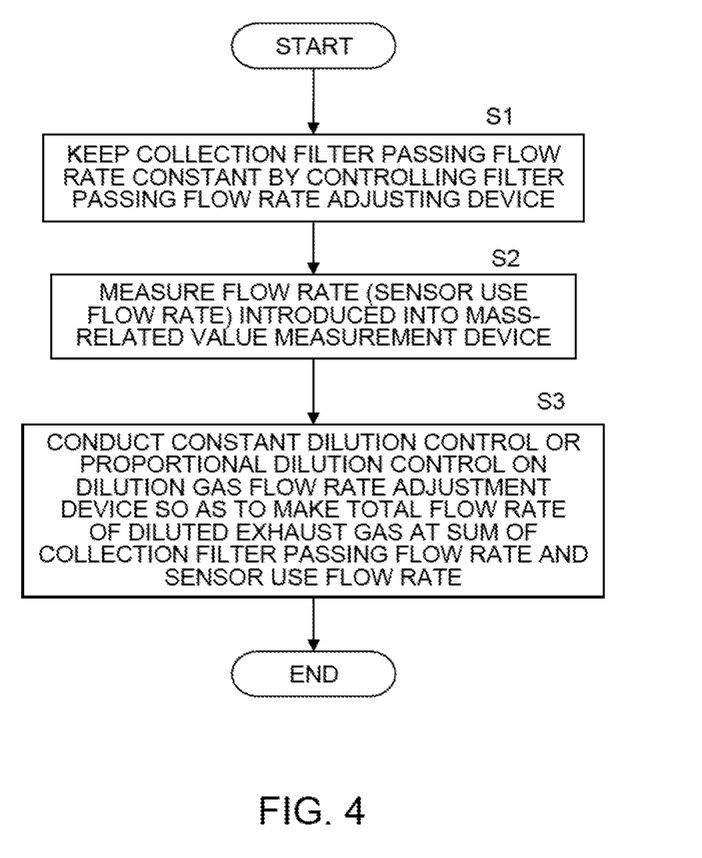
FIG. 4 is a flow chart showing a part of an operation of a control part in this embodiment.

Based on the measured values, the control part 81 outputs a control signal to the dilution gas flow rate adjusting device 2, more concretely, the piezoelectric valve 21 and conducts a constant dilution control or a proportional dilution control on the air introducing flow rate so as to be a total flow rate of the diluted exhaust gas at a summation of the collection filter passing flow rate and the sensor use flow rate (step S3 in FIG. 4).

The constant dilution control is to control the air introducing flow rate so as to be a ratio between the flow rate of the exhaust gas divided from the exhaust pipe (E) and the air introduction flow rate at a constant value, more specifically to make the dilution ratio constant. The proportional dilution control is to control the air introducing flow rate so as to introduce the exhaust gas at a constant flow rate ratio relative to a total flow rate of the exhaust gas flowing in the exhaust pipe (E).

As mentioned, in a state that the flow rate of each part is adjusted by the control part 81, the information processing part 82 automatically or by an operator receives a measurement data (hereinafter also called as a mass actually measured data) that is the mass of the particulate matters collected by the collection filter 61 during a predetermined period while the engine is in operation by means of the filter combustion method. The mass actually measured data indicates a total mass of the particulate matters during a period of collecting the particulate matters while the engine is in operation.

In addition, the information processing part 82 obtains the mass-related value measurement data, namely a value of the detected signal from the SOF measurement system 51 and the soot measurement system 52, output by the mass-related value measurement device 5 at a minute sampling time one after another continuously. Then, the mass of the SOF and the mass of the soot per unit flow rate of the exhaust gas are calculated from the detected signal value at each sampling time, and the calculated mass of the SOF and the calculated mass of the soot are added and then multiplied by a flow rate of the exhaust gas introduced into the collection filer 61 at the sampling time. The mass-related value measurement data with which the above process is provided is a time series change data of the mass-related value.

Then the information processing part 82 calculates a correlation between the mass value of the particulate matters shown by the mass actually measured data and the time integrated value of the mass-related value measurement data during a period while the particulate matters are collected by the collection filter 61. The correlation is, for example, a ratio of the value of the mass-related value measurement data to the time integrated value of the mass-related value measurement data.

Figure 5:
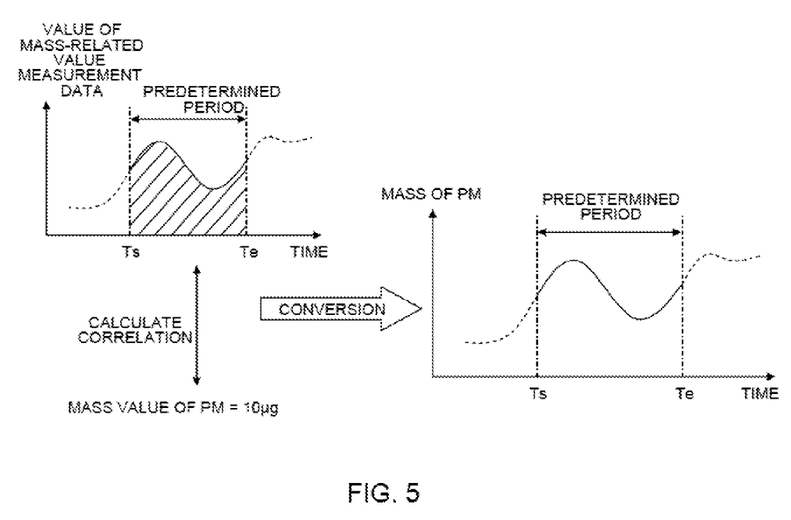
FIG. 5 is an explanatory view to help understanding of a method for measuring particulate matters in this embodiment.

Finally, as shown in FIG. 5, the information processing part 82 converts the mass-related value measurement data into the time series change data of the mass or the concentration of the particulate matters contained in the exhaust gas based on the above-mentioned correlation and outputs the converted value to a display or the like.

Since the time series change data of the mass of the particulate matters is a calibrated mass-related value measurement data continuously measured substantially in real time data based on the correlation to the actually measured mass of the particulate matters directly measured by the use of the filter mass method, and is calculated by the use of, so called, the correlation calculated for each operation of the engine, it becomes very reliable unlike with a conventional fixed correlation obtained under a static condition completely different from a dynamic condition such as running on a road.

In addition, in this embodiment, since the flow rate passing the collection filter 61 is made constant on a constant basis and the flow rate required for sampling by the mass-related value measurement device 5 is secured to be constant by controlling the flow rate of the diluted exhaust gas that is a mixture of the exhaust gas and the air with a process of increasing or decreasing the flow rate of the air for dilution, it is possible to preferably avoid a measurement error due to lack of the flow rate. Furthermore, in this embodiment, since the flow rate passing the collection filter 61 is made at a constant value determined by the regulation, it becomes possible to conduct a highly accurate measurement without correcting the amount of the particulate matters collected by the collection filter 61.

Second Embodiment

In the second embodiment, a hardware configuration is the same as that of the first embodiment, however, a software configuration, namely, an operation of the computer is different. Then an explanation is focused on the difference. The control part 81 of the computer 8 in this embodiment measures the sensor use flow rate just as the first embodiment (step S11 in FIG. 6). Next, the total flow rate of the flow rate of the diluted exhaust gas introduced into the mass-related value measurement device 5 and the flow rate of the diluted exhaust gas passing the collection filter 61 (the collection filter passing flow rate) is kept at a constant value on a constant basis by controlling the mass flow controller 73 of the filter passing flow rate adjusting device 7. Namely, since the flow rate (the sensor use flow rate) of the diluted exhaust gas introduced into the mass-related value measurement device 5 fluctuates due to a pressure change, the control part 81 outputs a command signal to the mass flow controller 73 while obtaining the measurement value of the sensor use flow rate and adjusts the collection filter passing flow rate so as to compensate the fluctuation and controls the total flow rate to be constant (step S12 in FIG. 6).

Figure 6:
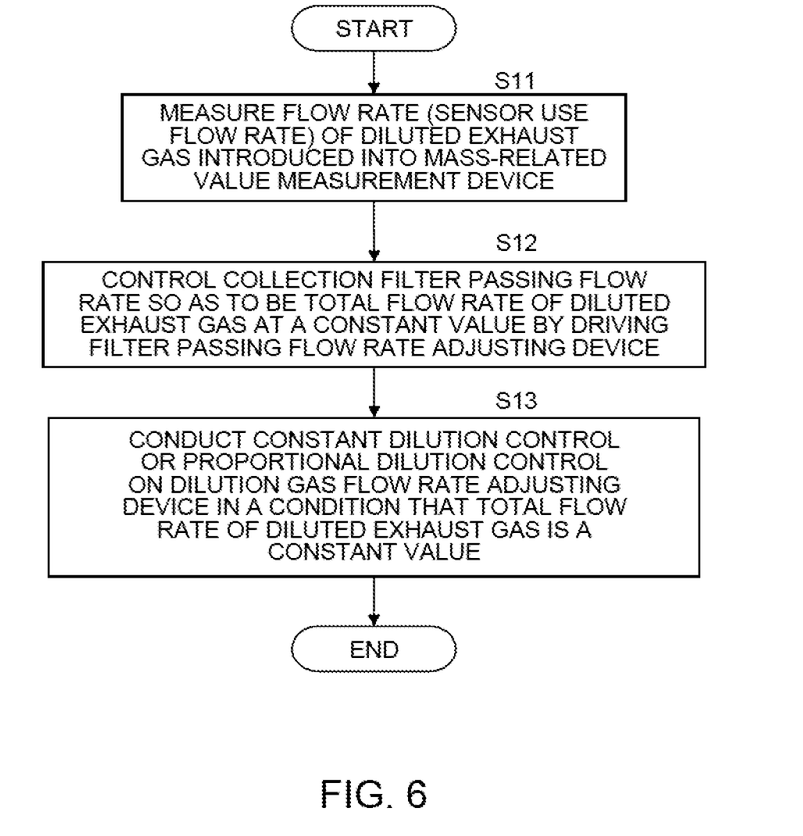
FIG. 6 is a flow chart showing a part of an operation of a control part in a second embodiment of this invention.

Meanwhile, the control part 81 drives the piezoelectric valve 21 of the dilution gas flow rate adjusting device 2 and conducts the above-mentioned constant dilution control or the proportional dilution control on the air introducing flow rate introduced into the mixer 1 (step S13 in FIG. 6).

Since a later operation of the information processing part 82 is almost the same as that of the first embodiment, an explanation will be omitted.

In accordance with this arrangement, just as the above-mentioned embodiment, it is possible to detect the concentration (mass) of the particulate matters of the exhaust gas discharged from the automobile running on a road generally in real time. Furthermore, in this embodiment, since the flow rate (the total flow rate of the collection filter passing flow rate and the sensor use flow rate) of the diluted exhaust gas is kept constant on a constant basis without any fluctuation just as the first embodiment, it is possible to obtain an effect that the constant dilution control or the proportional dilution control of the air introducing flow rate can be conducted easily and accurately.

The present claimed invention is not limited the above-mentioned embodiment.

For example, the predetermined period for measurement may be all the period from a start to an end while the automobile is in operation, or may be a part of the period.

The mass-related value measurement device is not limited to the above-mentioned DC sensor or the hydrogen flame ionization detector (FID), and may be, for example, an ELPI or an SMPS, and the flow rate may be controlled not by the venturi but by a constant volume pump.

In addition, it is a matter of course that the present claimed invention is not limited to the above-mentioned embodiment and may be variously modified without departing from a spirit of the invention.

POSSIBLE APPLICATIONS IN INDUSTRY

With this invention applied to, it is possible to continuously measure a change of the mass of the particulate matters contained in the exhaust gas with a simple arrangement under a dynamic driving situation such that an automobile is running on a road.

EXPLANATION OF CODES

100 . . . particulate matter measurement device
1 . . . mixer
2 . . . dilution gas flow rate adjusting device
22 . . . second measurement part
5 . . . mass-related value measurement device
61 . . . collection filter
7 . . . filter passing flow rate adjusting device
81 . . . control part
82 . . . information processing part
E . . . exhaust pipe
Ia . . . dilution gas introduction inlet

The invention claimed is:

1. A particulate matter measurement device comprising:
a mixer that is connected to an exhaust pipe of an automobile and connected to a dilution gas introducing inlet and that mixes an exhaust gas from an engine of the automobile with a dilution gas so as to dilute the exhaust gas,
a particulate matter sensor into which a part of the diluted exhaust gas diluted by the mixer is introduced and that continuously measures a mass-related value indirectly indicating a mass of particulate matters contained in the diluted exhaust gas,
a collection filter through which the remainder of the diluted exhaust gas passes and that collects the particulate matters contained in the remainder of the diluted exhaust gas,
a valve that adjusts a flow rate of the dilution gas introduced into the mixer,
a mass flow controller that adjusts a flow rate of the diluted exhaust gas passing, the collection filter, and
at least one controller programmed to keep a flow rate of the diluted exhaust gas passing the collection filter at a constant value by controlling the mass flow controller, to secure a necessary flow rate of the diluted exhaust gas introduced into the particulate matter sensor by controlling the valve, to calculate a correlation between a mass measurement value of the particulate matters collected by the collection filter during a predetermined period while the engine is in operation and a time integrated value of the mass-related value measurement data during the predetermined period, as being a time series change data of the mass-related value measured by the particulate matter sensor, and to convert the mass-related value measurement data to the time series change data of the mass of the particulate matters based on the correlation.

2. The particulate ma measurement device described in claim 1 wherein the particulate matter measurement device is loaded on the automobile which runs on a road and measures the particulate matters in the exhaust gas while the automobile is running.

3. A particulate matter measurement device comprising:
a mixer that is connected to an exhaust pipe of an automobile and connected to a dilution gas introducing inlet and that mixes an exhaust gas from an engine of the automobile with a dilution gas so as to dilute the exhaust gas,
a particulate matter sensor into which a part of the diluted exhaust gas diluted by the mixer is introduced and that continuously measures a mass-related value indirectly indicating a mass of particulate matters contained in the diluted exhaust gas,
a collection filter through which the remainder of the diluted exhaust gas passes and that collects the particulate matters contained in the remainder of the diluted exhaust gas,
a valve that adjusts a flow rate of the dilution gas introduced into the mixer,
a mass flow controller that adjusts a flow rate of the diluted exhaust gas passing the collection filter, and at least one controller programmed to keep as sum of the flow rate of the diluted exhaust was introduced into the particulate matter sensor and the flow rate of the diluted exhaust gas passing the collection filter at a constant value by controlling the mass flow controller based on the flow rate of the diluted exhaust gas introduced into the particulate matter sensor, to calculate a correlation between a mass measurement value of the particulate matters collected by the collection filter during a predetermined period while the engine is in operation and a time integrated value of the mass-related value measurement data during the predetermined period as being a time series change data of the mass-related value measured by the particulate matter sensor, and to convert the mass-related value measurement data to the time series change data of the mass of the particulate matters based on the correlation.

4. A particulate matter measurement device comprising:
a mixer that is connected to an exhaust pipe of an automobile and connected to a dilution gas introducing inlet and that mixes an exhaust gas from an engine of the automobile with a dilution gas so as to dilute the exhaust gas,
a sensor into which a part of the diluted exhaust gas diluted by the mixer is introduced and that continuously measures a mass-related value indirectly indicating a mass of particulate matters contained in the diluted exhaust gas,
a collection filter through which the remainder of the diluted exhaust gas passes and that collects the particulate matters contained in the remainder of the diluted exhaust gas,
a dilution gas flow rate controller that adjusts a flow rate of the dilution gas introduced into the mixer,
a filter passing flow rate controller that adjusts a flow rate of the diluted exhaust gas passing the collection filter, and
at least one controller programmed to keep a flow rate of the diluted exhaust gas passing the collection filter at a constant value by controlling the filter passing flow rate controller, to secure a necessary flow rate of the diluted exhaust gas introduced into the sensor by controlling the dilution gas flow rate controller, to calculate a correlation between a mass measurement value of the particulate matters collected by the collection filter during a predetermined period while the engine is in operation and a time integrated value of the mass-related value measurement data during the predetermined period as being a time series change data of the mass-related value measured by the sensor, and to convert, the mass-related value measurement data to the time series change data of the mass of the particulate matters based on the correlation.

5. The particulate matter measurement device described in claim 4 wherein the particulate matter measurement device is loaded on the automobile which runs on a road and measures the particulate matters in the exhaust gas while the automobile is running.

6. A particulate matter measurement device comprising:
a mixer that is connected to an exhaust pipe of an automobile and connected to a dilution gas introducing inlet and that mixes an exhaust gas from an engine of the automobile with a dilution gas so as to dilute the exhaust gas,
a sensor into which a part of the diluted exhaust as diluted by the mixer is introduced and that continuously measures a mass-related value indirectly indicating a mass of particulate matters contained in the diluted exhaust gas,
a collection filter through which the remainder of the diluted exhaust gas passes and that collects the particulate matters contained in the remainder of the diluted exhaust gas,
a dilution gas flow rate controller that adjusts a flow rate of the dilution gas introduced into the mixer,
a filter passing flow rate controller that adjusts as flow rate of the diluted exhaust gas passing the collection filter, and
at least one controller programmed to keep a sum of the flow rate of the diluted exhaust gas introduced into the sensor and the flow rate of the diluted exhaust gas passing the collection filter at a constant value by controlling the filter passing flow rate controller based on the flow rate of the diluted exhaust as introduced into the sensor, to calculate a correlation between a mass measurement value of the particulate matters collected by the collection filter during a predetermined period while the engine is in operation and a time integrated value of the mass-related value measurement data during the predetermined period as being a time series change data of the mass-related value measured by the sensor, and to convert the mass-related value measurement data to the time series change data of the mass of the particulate matters based on the correlation.

7. A particulate matter measurement device comprising:
a mixer that is connected to an exhaust pipe of an automobile and connected to a dilution gas introducing inlet and that mixes an exhaust gas from n engine of the automobile with a dilution gas so as to dilute the exhaust gas,
a sensor into which a part of the diluted exhaust gas diluted by the mixer is introduced and that continuously measures a mass-related value indirectly indicating a mass of particulate matters contained in the diluted exhaust gas,
a collection filter through which the remainder of the diluted exhaust gas passes and that collects the particulate matters contained in the remainder of the diluted exhaust gas,
a valve that adjusts a flow rate of the dilution gas introduced into the mixer,
a filter passing flow rate controller that adjusts a flow rate of the diluted exhaust gas passing the collection filter, and
at least one controller programmed to keep a flow rate of the diluted exhaust gas passing the collection filter at a constant value by controlling the filter passing flow rate controller, to secure a necessary flow rate of the diluted exhaust gas introduced into the sensor by controlling the valve, to calculate a correlation between a mass measurement value of the particulate matters collected by the collection filter during a predetermined period while the engine is in operation and a time integrated value of the mass-related value measurement data during the predetermined period as being a time series change data of the mass-related value measured by the sensor, and to convert the mass-related value measurement data to the time series change data of the mass of the particulate matters based on the correlation.

8. The particulate matter measurement device described in claim 7 wherein the particulate matter measurement device is loaded on the automobile which runs on a road and measures the particulate matters in the exhaust gas while the automobile is running.

9. A particulate matter measurement device comprising:
a mixer that is connected to an exhaust pipe of an automobile and connected to a dilution gas introducing inlet and that mixes an exhaust gas from an engine of the automobile with a dilution gas so as to dilute the exhaust gas, a sensor into which a part of the diluted exhaust gas diluted by the mixer is introduced and that continuously measures a mass-related value indirectly indicating a mass of particulate matters contained in the diluted exhaust gas, a collection filter through which the remainder of the diluted exhaust gas passes and that collects the particulate matters contained in the remainder of the diluted exhaust gas, a valve that adjusts a flow rate of the dilution gas introduced into the mixer, a filter passing flow rate controller that adjusts a flow rate of the diluted exhaust gas passing the collection filter, and at least one controller programmed to keep a sum of the flow rate of the diluted exhaust gas introduced into the sensor and the flow rate of the diluted exhaust gas passing the collection filter at a constant value by controlling the filter passing flow rate controller based on the flow rate of the diluted exhaust gas introduced into the sensor, to calculate a correlation between a mass measurement value of the particulate matters collected by the collection filter during a predetermined period while the engine is in operation and a time integrated value of the mass-related value measurement data during the predetermined period as being a time series change data of the mass-related value measured by the sensor, and to convert the mass-related value measurement data to the time series change data of the mass of the particulate matters based on the correlation.

10. A particulate matter measurement device comprising a dilutor that is connected to an exhaust pipe of an automobile and connected to a dilution gas introducing inlet and that mixes an exhaust gas from an engine of the automobile with a dilution gas so as to dilute the exhaust gas, a mass-related value measurement device into which a part of the diluted exhaust gas diluted by the dilutor is introduced and that continuously measures a mass-related value indirectly indicating a mass of particulate matters contained in the diluted exhaust gas, a collection filter through which the remainder of the diluted exhaust gas passes and that collects the particulate matters contained in the remainder of the diluted exhaust gas, a dilution gas flow rate adjusting device that adjusts a flow rate of the dilution gas introduced into the dilutor, a filter passing flow rate adjusting device that adjusts a flow rate of the diluted exhaust gas passing the collection filter, a control part that keeps a flow rate of the diluted exhaust gas passing the collection filter at a constant value by controlling, the filter passing flow rate adjusting device and that secures a necessary flow rate of the diluted exhaust gas introduced into the mass-related value measurement device by controlling the dilution gas flow rate adjusting device, and an information processing part that calculates a correlation between a mass measurement value of the particulate matters collected by the collection filter during a predetermined period while the engine is in operation and a time integrated value of the mass-related value measurement data during the predetermined period as being a time series change data of the mass-related value measured by the mass-related value measurement device and that converts the mass-related value measurement data to the time series change data of the mass of the particulate matters based on the correlation.

11. The particulate matter measurement device described in claim 1 wherein the particulate matter measurement device is loaded on the automobile which runs on a road and measures the particulate matters in the exhaust gas while the automobile is running.

12. A particulate matter measurement device comprising a dilutor that is connected to an exhaust pipe of an automobile and connected to a dilution gas introducing inlet and that mixes an exhaust gas from an engine of the automobile with a dilution gas so as to dilute the exhaust gas, a mass-related value measurement device into which a part of the diluted, exhaust gas diluted by the dilutor is introduced and that continuously measures a mass-related value indirectly indicating a mass of particulate matters contained in the diluted exhaust gas, a collection filter through which the remainder of the diluted exhaust gas passes and that collects the particulate matters contained in the remainder of the diluted exhaust gas, a dilution gas flow rate adjusting device that adjusts a flow rate of the dilution gas introduced into the dilutor, a filter passing flow rate adjusting device that adjusts a flow rate of the diluted exhaust gas passing the collection filter, a control part that keeps a sum of the flow rate of the diluted exhaust gas introduced into the mass-related value measurement device and the flow rate of the diluted exhaust gas passing the collection filter at a constant value by controlling the filter passing flow rate adjusting device based on the flow rate of the diluted exhaust gas introduced into the mass-related value measurement device, and an information processing part that calculates a correlation between a mass measurement value of the particulate matters collected by the collection filter during a predetermined period while the engine is in operation and a time integrated value of the mass-related value measurement data during the predetermined period as being a time series change data of the mass-related value measured by the mass-related, value measurement device and that converts the mass-related value measurement data to the time series change data of the mass of the particulate matters based on the correlation.

* * * * *